US011205516B2

(12) United States Patent
Lieberman

(10) Patent No.: US 11,205,516 B2
(45) Date of Patent: Dec. 21, 2021

(54) MACHINE LEARNING SYSTEMS AND METHODS FOR ASSESSING MEDICAL INTERVENTIONS FOR UTILIZATION REVIEW

(71) Applicant: Daniel M. Lieberman, Phoenix, AZ (US)

(72) Inventor: Daniel M. Lieberman, Phoenix, AZ (US)

( * ) Notice: Subject to any disclaimer, the term of this patent is extended or adjusted under 35 U.S.C. 154(b) by 0 days.

(21) Appl. No.: 16/122,100

(22) Filed: Sep. 5, 2018

(65) Prior Publication Data

US 2020/0075164 A1 Mar. 5, 2020

(51) Int. Cl.
*G16H 50/20* (2018.01)
*G06N 20/00* (2019.01)
*G06N 5/04* (2006.01)
*G16H 30/40* (2018.01)

(52) U.S. Cl.
CPC .............. *G16H 50/20* (2018.01); *G06N 20/00* (2019.01); *G06N 5/046* (2013.01); *G16H 30/40* (2018.01)

(58) Field of Classification Search
CPC ................................ G06N 20/00; G06F 19/34
See application file for complete search history.

(56) References Cited

U.S. PATENT DOCUMENTS

| | | | |
|---|---|---|---|
| 4,872,122 A | 10/1989 | Altschuler et al. | |
| 5,005,143 A | 4/1991 | Altshuler et al. | |
| 5,486,999 A | 1/1996 | Mebane | |
| 5,517,405 A | 5/1996 | McAndrew et al. | |
| 6,687,685 B1 | 2/2004 | Sadeghi et al. | |
| 8,296,247 B2 | 10/2012 | Zhang et al. | |
| 2015/0073943 A1* | 3/2015 | Norris | G06F 16/24575 705/26.63 |
| 2016/0026762 A1* | 1/2016 | Radhakrishnan | G06F 19/3418 705/3 |
| 2017/0091386 A1* | 3/2017 | Varkuti | G06F 19/321 |

OTHER PUBLICATIONS

M.S. Hossain and G. Muhammad, "Healthcare big data voice pathology assessment framework", IEEE Access, vol. 4, pp. 7806-7815, Nov. 8, 2016. (Year: 2016).*

P. Nadkarni, L. Ohno-Machado, and W. Chapman, "Natural language processing: an introduction", J. Am. Med. Inform. Assoc., vol. 18, 2011, pp. 544-551. (Year: 2011).*

(Continued)

*Primary Examiner* — Vincent Gonzales
(74) *Attorney, Agent, or Firm* — Daniel R. Pote

(57) ABSTRACT

Systems and methods are disclosed for determining the appropriateness of medical interventions. In one embodiment, a machine learning system for determining the appropriateness of a selected medical intervention includes health-related data sources, the health-related data sources providing at least one data file of a first type, and a second data file of a second type. A machine learning module is configured to receive the first and second data files, perform a normalization procedure on at least one of the first and second data files, and apply at least one previously trained machine learning model to the normalized data files to produce a prediction output. The prediction output may include a confidence level associated with an appropriateness of the selected medical intervention.

20 Claims, 10 Drawing Sheets

Example Supervised Training Methods

(56) References Cited

OTHER PUBLICATIONS

G. Yu and JJ. Slotine, "Audio classification from time-frequency texture", IEEE Int'l Conf. on Acoustics, Speech, and Sig. Processing 2009, pp. 1677-1680. (Year: 2009).*

Y. Deng and P. Bentley, "A robust heart sound segmentation and classification algorithm using wavelet decomposition and spectrogram", Workshop Classifying Heart Sounds, La Palma, Canary Islands, 2012, 6 pages. (Year: 2012).*

D. Giri et al., "Automated diagnosis of Coronary Artery Disease affected patients using LDA, PCA, ICA and Discrete Wavelet Transform", Knowledge-Based Systems, vol. 37, 2013, pp. 274-282. (Year: 2013).*

U.R. Acharya et al., "Automated detection of coronary artery disease using different durations of ECG segments with convolution neural network", Knowledge-Based Systems, vol. 132, 2017, pp. 62-71. (Year: 2017).*

Kang, Seokho et al. "An efficient and effective ensemble of support vector machines for anti-diabetic drug failure prediction", Expert systems with applications 42, 2015, pp. 4265-4273. (Year: 2015).*

Blackburn, George et al., "Expert Panel on Weight Loss Surgery: Executive Report Update", Obsesity 17, Feb. 2009, pp. 842-862. (Year: 2009).*

Shekelle, Paul et al., "The reproducibility of a method to identify the overuse and underuse of medical procedures", New England J. Medicine, Jun. 25, 1998, pp. 1888-1895. (Year: 1998).*

Nelson, Brent et al., "Computerized decision support for concurrent utilization review using HELP system", J. Amer. Med. Assoc., vol. 1, No. 4, Jul/Aug. 1994, pp. 339-352. (Year: 1994).*

Thottakkara, Paul et al., "Application of machine learning techniques to high-dimensional clinical data to forecast postoperative complications", PLoS ONE 11(5), May 27, 2016, 19 pages. (Year: 2016).*

Yermilov I, McGory ML, Shekelle PW, Ko CY, Maggard MA. Appropriateness criteria for bariatric surgery: beyond the NIH guidelines. Obesity. Aug. 2009;17(8):1521-7. (Year: 2009).*

McDonnell J, Meijler A, Kahan JP, Bernstein SJ, Rigter H. Panellist consistency in the assessment of medical appropriateness. Health Policy. Sep. 1, 1996;37(3):139-52. (Year: 1996).*

International Search Report, PCT/US19/47669, dated Sep. 23, 2019; 3 pgs.

Written Opinion, PCT/US19/47669, dated Sep. 23, 2019; 7 pgs.

* cited by examiner

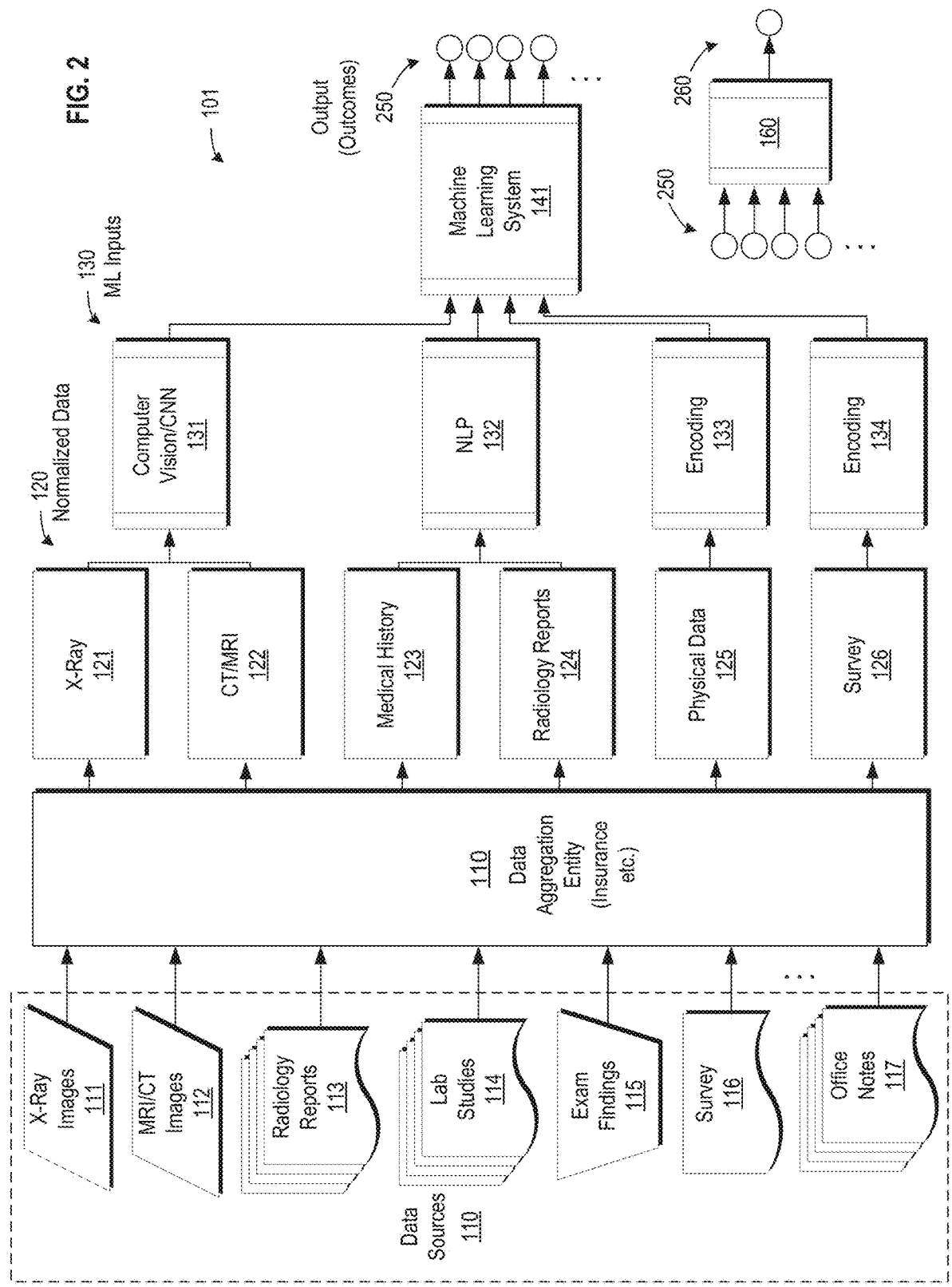

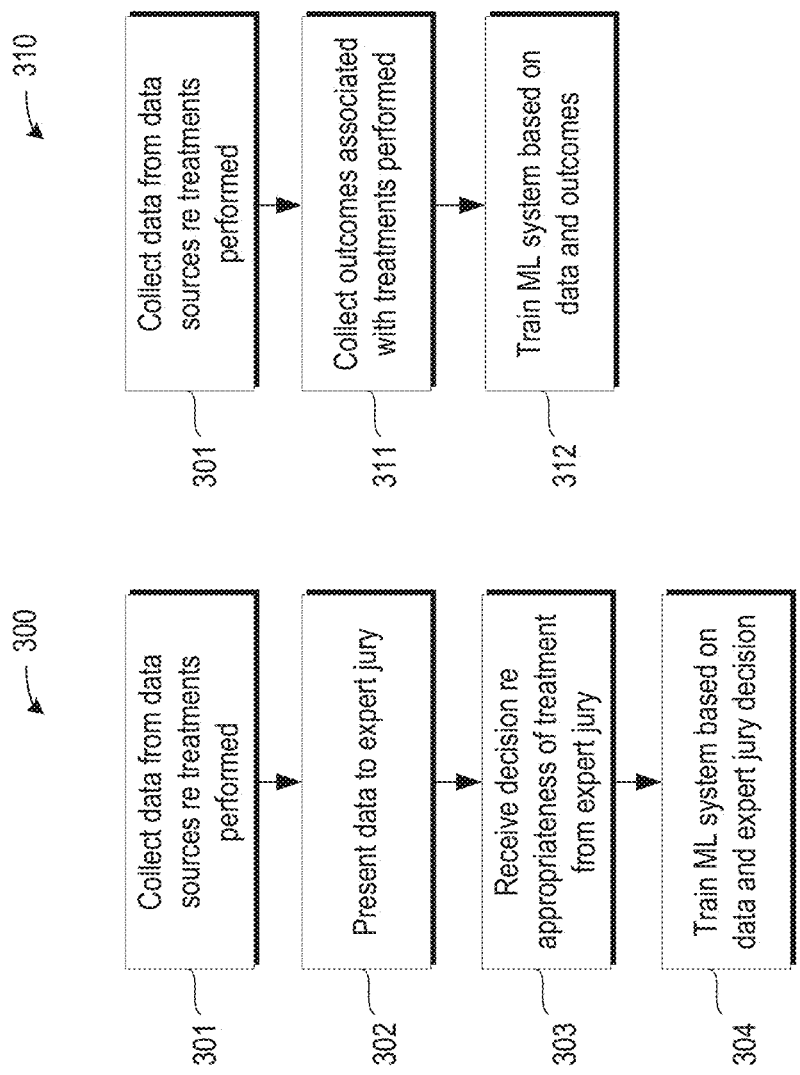

MACHINE LEARNING SYSTEMS AND METHODS FOR ASSESSING MEDICAL INTERVENTIONS FOR UTILIZATION REVIEW

TECHNICAL FIELD

The present invention relates, generally, to systems and methods for determining whether particular medical treatments are appropriate and, more particularly, to the application of machine learning techniques to the evaluation of such treatments and interventions.

BACKGROUND

Determining whether a particular medical invention is appropriate for a given patient continues to be challenging. Such determinations are important, however, as they can have a profound impact on patient health outcomes, healthcare costs, and other individual and societal factors.

In the context of healthcare insurance providers and other similarly situated entities, it is particularly desirable to avoid false-positives, i.e., instances in which a patient is incorrectly classified as a candidate and/or subjected to unnecessary medical interventions. Toward that end, health insurance providers often carry out a "utilization review" in which the insurer evaluates the medical necessity of a requested medical procedure for the purpose of providing preauthorization.

Even given recent advances in medical care, insurance case management techniques, and data analysis, healthcare costs (and consequently insurance premiums) continue to rise in an unsustainable fashion. This is due in part to the difficult of determining whether a requested medical intervention is appropriate for a particular individual under the circumstances.

Systems and methods are thus needed which overcome the limitations of the prior art. Various features and characteristics will also become apparent from the subsequent detailed description and the appended claims, taken in conjunction with the accompanying drawings and this background section.

BRIEF SUMMARY

Various embodiments of the present invention relate to systems and methods for, inter alia: i) using machine learning techniques to determine whether a selected medical intervention is necessary; ii) utilizing heterogeneous forms of aggregated data (such as imaging, lab studies, exam findings, survey information, and the like) as inputs to a machine learning system as described herein, ii) improving insurer utilization reviews using the machine learning systems described herein; iii) using multiple pre-trained artificial neural networks to implement the machine learning systems described herein; and iv) utilizing the machine learning systems described herein to determine whether a particular health care provider or physician is appropriate given the desired medical intervention.

Various other embodiments, aspects, and features are described in greater detail below.

BRIEF DESCRIPTION OF THE DRAWING FIGURES

Exemplary embodiments will hereinafter be described in conjunction with the following drawing figures, wherein like numerals denote like elements, and:

FIG. 2 is a schematic overview of an alternate system for assessing medical interventions in accordance with various embodiments;

FIGS. 3A and 3B are flowcharts illustrating various supervised training methods in accordance with various embodiments;

DETAILED DESCRIPTION

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate to systems and methods for applying machine learning techniques to the problem of determining the appropriateness of particular medical interventions. The disclosed techniques provide systems and methods for considering a wide range of heterogeneous data types (e.g., digital images, radiological reports, lab studies, exam findings, survey information, and the like) that are normalized for use as inputs to one or more machine learning systems. This normalization itself may leverage one or more machine learning modules, such as convolutional neural networks and the like.

While systems and methods are often described herein in the context of surgery and surgical procedures, the invention is not so limited, and may be used to predict the necessity of a wide range of invasive and non-invasive treatments. The term "medical intervention" therefore comprehends any form of treatment, ranging from medication to various non-invasive and/or invasive diagnostic procedures, performed to treat a one or more health conditions.

Figure 1:
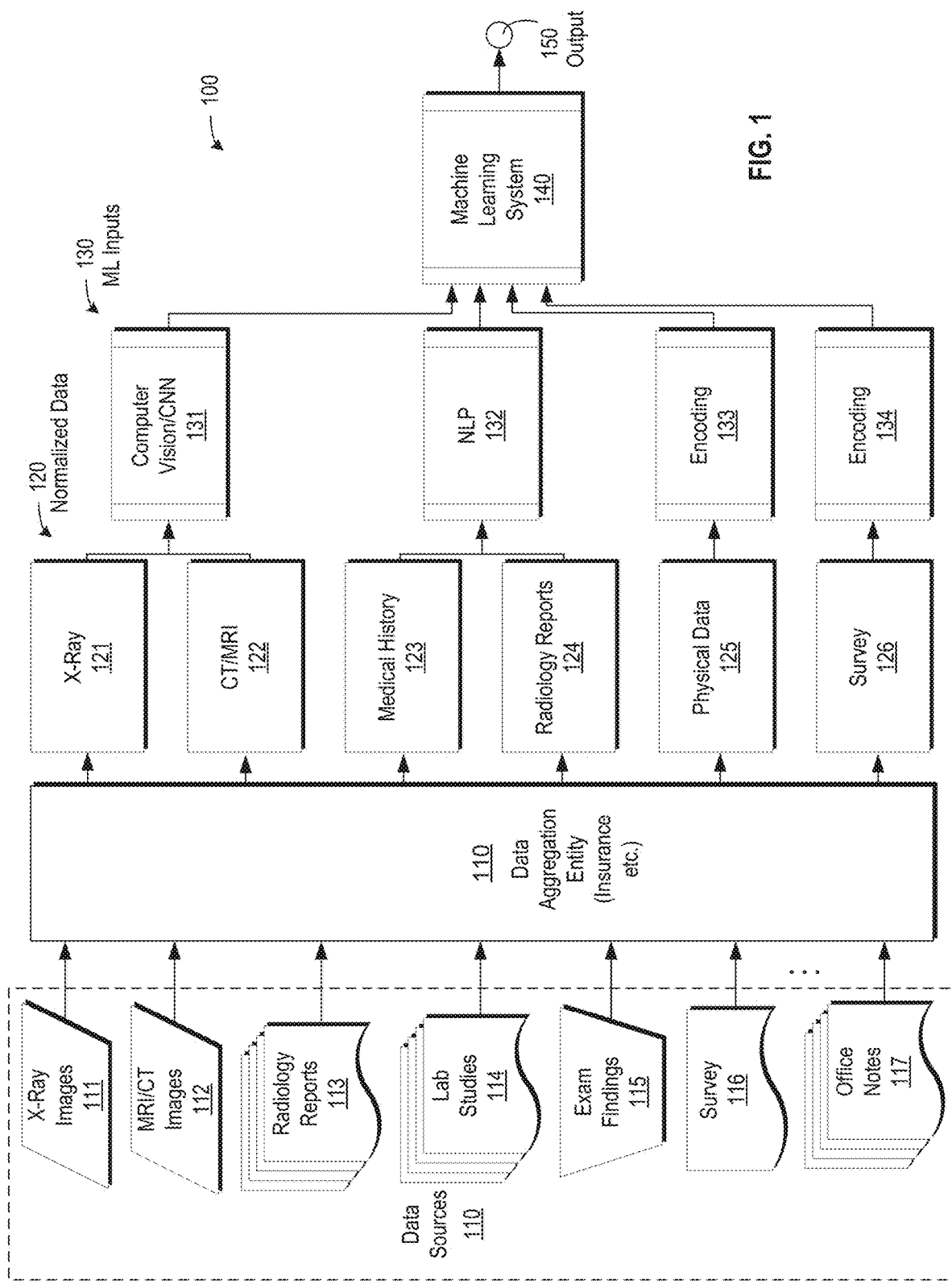
FIG. 1 is a schematic overview of a system for assessing medical interventions in accordance with various embodiments.

FIG. 1 is a schematic overview of a system 100 for assessing medical interventions in accordance with various embodiments. In general, system 100 includes a wide range of data sources 110 for generating medical-related information (referred to herein without loss of generality as "data files") that are provided to a data aggregation entity 110, which may correspond to an medical insurance company, a healthcare provider, or any other entity that might have access to a data sources 110. In some embodiments, entity 110 comprises multiple organizations, individuals, practices, etc. that agree to pool their individual data sources 110, which may be stored in a centralized location or distributed over any number of servers or other network architectures.

The various data files accumulated from data sources 110 are suitable normalized (as described further below) to produce normalized data 120. This data may then be further processed to produce machine language (ML) inputs 130. These inputs 130 are then provided to previously trained machine learning system 140 to produce a classification output 150 which, in various embodiments, corresponds to a probability level (e.g., within the range 0.0-1.0, inclusive) that a particular medical intervention is appropriate. As further described below, machine learning system 140 may be trained using outputs derived from a jury of experts (e.g., medical professionals qualified to make such determinations). Stated another way, system 100, as a whole, is trained to simulate the judgment of an expert panel with respect to whether a particular medical intervention is appropriate.

With continued reference to FIG. 1, data sources 110 may include any source of medical data now known or later developed. In the illustrated embodiment, without limitation, data sources 110 may include X-ray images 111 (e.g., anterior, posterior, lateral, or oblique images), MRI and/or CT images 112 (e.g., sectional images along various anatomic planes, and the parameters under which the images are obtained), radiology reports 113 (i.e., written assessments of an X-ray image), lab studies 114, exam findings 115, survey data 116, office notes 117, and the like.

Lab studies 114 may include, for example, data regarding serum, urine, cerebrospinal fluid, microbacteriological culture, and other bodily fluids. Data sources 110 may include other functional data such as ultrasound data, cardiac stress tests (chemical or exertional), pulmonary function data, renal function tests, electroencephalogram data, myelographical data, angiographical data, bone density data, and the like.

Images provided by data sources 110 may be stored and transferred in any convenient format, such as the standard Dicom format. Radiological reports 113 may be in the form of mixed numerical and text data, a PDF, or may be in the form of a fax print-out format. Lab studies 114 may also be in PDF, fax, or mixed numeral and text format. Office notes 117 may be in the form of structured or unstructured text, and exam findings 115 may be in the form of audio files (e.g., heart or lung sounds), or scalar values such as range of motion measurements.

As illustrated in FIG. 1, normalized data 120 may be produced by aggregating and processing data files from data sources 110. This normalized data 120 may be provided in a variety of forms as well, including, for example, X-rays 121, CT/MRI images 122, medical history 123, radiology reports 124, physical data 125, and survey data 126.

The normalized data 120 is then processed to produce a set of ML inputs 130 for machine learning system 140. In the illustrated embodiment, for example, normalized X-ray and CT/MRI data 121, 122 may be processed by a computer vision or convolutional neural network system 131 to extract features from those images (e.g., anatomical dimensions, etc.). Similarly, normalized medical history data 123 and radiology reports 124 may be processed by a natural language processing system 132. Finally, physical data 125 and survey data 126 may be encoded by respective encoding modules 133 and 134.

Figure 4A:
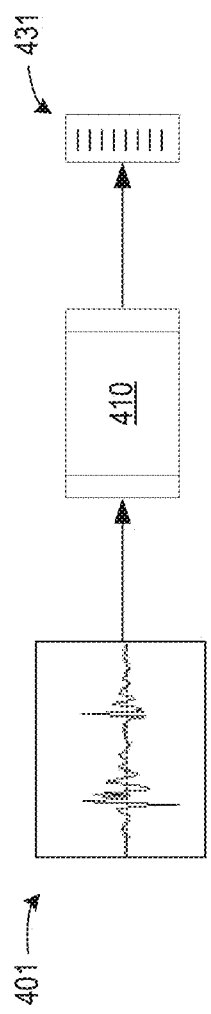
FIGS. 4A-4C illustrate example data normalization systems in accordance with various embodiments.
Figure 4B:
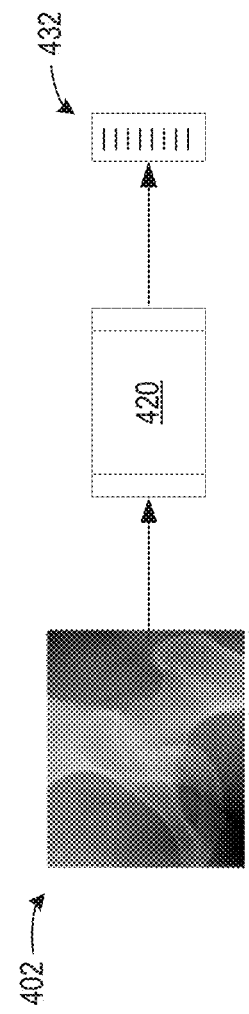
Figure 4C:
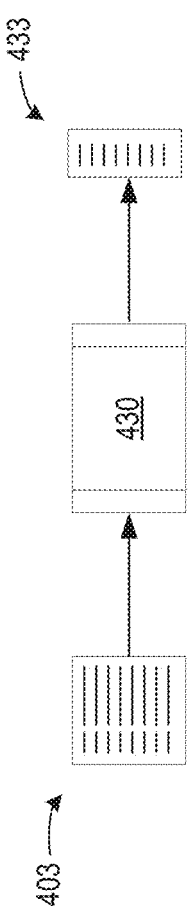

Referring briefly to FIGS. 4A-4C, various exemplary normalization systems are illustrated. In FIG. 4A, for example, a data file comprising time-varying real values 401 is processed by a module 410 to produce a vector of real values 431. In an embodiment in which data file 401 consists of a heart or lung audio recording, module 410 may produce a vector 431 that characterizes the frequency distribution over time of the audio information.

FIG. 4B illustrates a second example in which a two dimensional image file 402 having some appropriate bit depth is processed by module 420 to produce a vector 432. In one embodiment, for example, module 420 performs image feature extraction to determine one or more geometric features of image 402 (e.g., distance between adjacent bone structures, curvatures of anatomical features, and the like).

FIG. 4C illustrates a third example in which a structured or unstructured text file (e.g., a written report, office notes, etc.) are processed by a natural language processing module 430 to produce a vector 433 that extracts meaningful information from such text. In some embodiments, text string data is converted to appropriate numerical data (e.g., a numerical indicator of pain level based on a text assessment of an individual's pain level).

While FIG. 1 illustrates a system that produces an output 150 indicative of whether a particular medical intervention is appropriate (e.g., a real probability value in the range of 0.0-1.0), FIG. 2 presents an alternate system for assessing medical interventions in accordance with various embodiments. That is, instead using a binary classifier for machine learning system 140, FIG. 2 illustrates a system in which outcomes 250 are used for training. Such outcomes may include, for example, patient satisfaction level (expressed numerically on a suitable scale), health complications (expressed as categorical data), cost per episode (in monetary units), functional status (e.g., the extent to which the patient has recovered to full functionality), and the need for ongoing additional treatments.

In some embodiments, the outputs 250 may be fed into a secondary machine learning module 160 that is trained to determine whether a particular medical intervention is indicated given the expected outcomes.

In general, empirical testing of machine learning systems in accordance with the present subject matter has shown that such systems exhibit predictive accuracies that meet and often exceed those of providers utilizing heuristic and other traditional techniques.

The machine learning systems of FIGS. 1 and 2 may be advantageously utilized by a number of data aggregation entities, including individual surgeons, healthcare providers, and healthcare insurance companies. For example, the systems illustrated above may be used in the context of a utilization review performed by a healthcare insurance company. In such a utilization review, a patient meets with the healthcare provider or surgeon, and as a result of this consultation, the provider and patient agree that the patient is a candidate a particular medical intervention. Next, a preauthorization request is sent by the provider to the insurer. This request may be accompanied by additional data relevant to the preauthorization requests, such as X-rays, lab results, etc. The insurer may represent any entity configured to cover healthcare costs for the patient, including private insurers, government payers, health maintenance organizations (HMOs), and self-insured employers. The insurer processes the available data sources, using the various machine learning systems and methods described above, to make a determination as to whether the requested surgical procedure is appropriate. Depending upon this determination, insurer either approves or denies the preauthorization request.

FIGS. 3A and 3B are flowcharts illustrating various supervised training methods in accordance with various embodiments. More particularly, FIG. 3A illustrates a method 300 corresponding to the system of FIG. 1, which begins (at 301) with the collection of data from various data sources 110 based on treatments previously performed. This data is then presented (at 302) to an expert jury comprising one or more individuals qualified to assess the data sources to determine whether the particular treatment performed was appropriate in a particular case. The jury then renders a decision as to the appropriateness of the treatment (303), and that data (i.e., a corpus of supervised training data) is then used to train machine learning system 140. In accordance with another embodiment, data is collected from cases actually performed by a trusted expert. For example, the data collected may include all total hip cases performed by three doctors known to be particularly proficient at such cases. This collection then effectively serves as the jury. The machine learning system, after training, can then decide whether one of the trust surgeons would have done the procedure as presented.

FIG. 3B illustrates an alternate method 310, corresponding to the system illustrated in FIG. 2, in which data is collected from data sources (301), the outcomes associated with a treatment is collected (311), and the machine learning system 141 is trained using that data. That is, the outcomes are provided to the outputs 250 of machine learning system 141 during supervised training.

As discussed briefly above, one of the advantages of systems in accordance with the present invention is the use of heterogeneous data—i.e., a wide range of data types, ranging from images, sounds, lab studies, and the like—which is then normalized in a way that can be used to train the relevant machine learning models.

Figure 5:
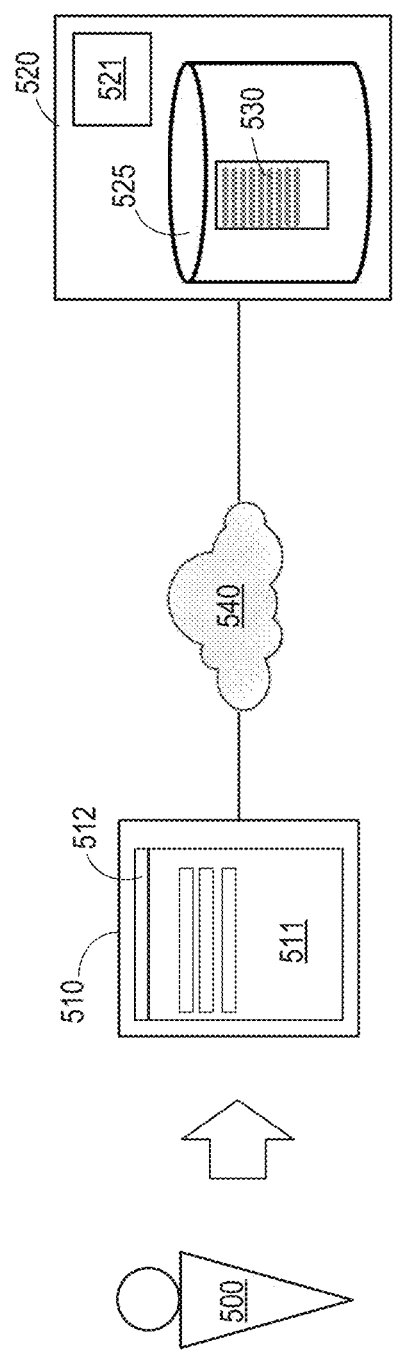
FIG. 5 illustrates a method of acquiring survey data in accordance with one embodiment.

FIG. 5 is a schematic overview of a system for generating survey responses (e.g., data 126 in FIGS. 1 and 2) in accordance with various embodiments. More particularly, in this web-based example, a patient 500 interacts with a survey user interface 512 displayed via a computing device 510 (e.g., a desktop computer, laptop computer, tablet device, smart-phone, or the like). Survey user interface 512 includes a series of questions or prompts 511 configured to elicit responses from patient 500. These responses may take a variety of forms, for example, short answer (text), yes/no selection (Boolean), numeric values (integer or floating point), voice recordings, images, and biometric input data. Responses may be selected and/or entered using a variety of user interface elements known in the art, such as radio buttons, drop-down menus, text entry boxes, buttons, and date fields. As described in further detail below, survey questions 511 may relate to, for example, basic patient information (age, weight, height, etc.), past treatments, exercise level, past accidents, current symptoms, pain levels, and other such questions that might be used as input to a machine learning system.

In accordance with another embodiment, the system includes an AI system configured to engage in an interactive conversation with a patient. In this way, the AI system administers a survey, which then serves as the input for another neural network system. Thus, the AI module acts as the agent conducts the survey.

In the illustrated embodiment, user interface 512 is a web page or collection of web pages displayed in a web browser operating on device 510 and provided by a survey module 521 (e.g., a web service with associated back end databases, software, etc.) located at a remote server 520. Server 520 may be associated with, for example, an insurance provider, a health care provider, or an individual surgeon.

Interaction of patient 500 with survey user interface 512 causes survey results 530 to be generated and transmitted over network 140 (e.g., the Internet) to server 520, whereupon they are stored within a database 525. Survey results 530 are preferably transmitted in a secure fashion, e.g., via an https protocol.

In some embodiments, data entered by patient 500 may be transformed to produce survey results 530 that are better configured for use by a machine learning system. For example, one of the questions 511 may be an open-ended question such as, "how would you describe your back pain right now." In response, the patient may be asked to type (or speak) a response, which is then provided to a speech recognition system and/or natural language processing system as illustrated in FIGS. 1 and 2.

It will be appreciated that the particular architecture illustrated in FIG. 5 is not intended to be limiting. The components of the illustrated system (e.g., database 525, module 521, and server 520) may be distributed between multiple remote locations and parties. Furthermore, survey user interface 512 need not be implemented as a web-based system, but might be a stand-alone program running on device 510 that stores survey results 530 locally for later transmission and processing. In some embodiments, survey user interface 512 is an application that can be downloaded to device 510 via a publicly accessible app store.

Figure 6:
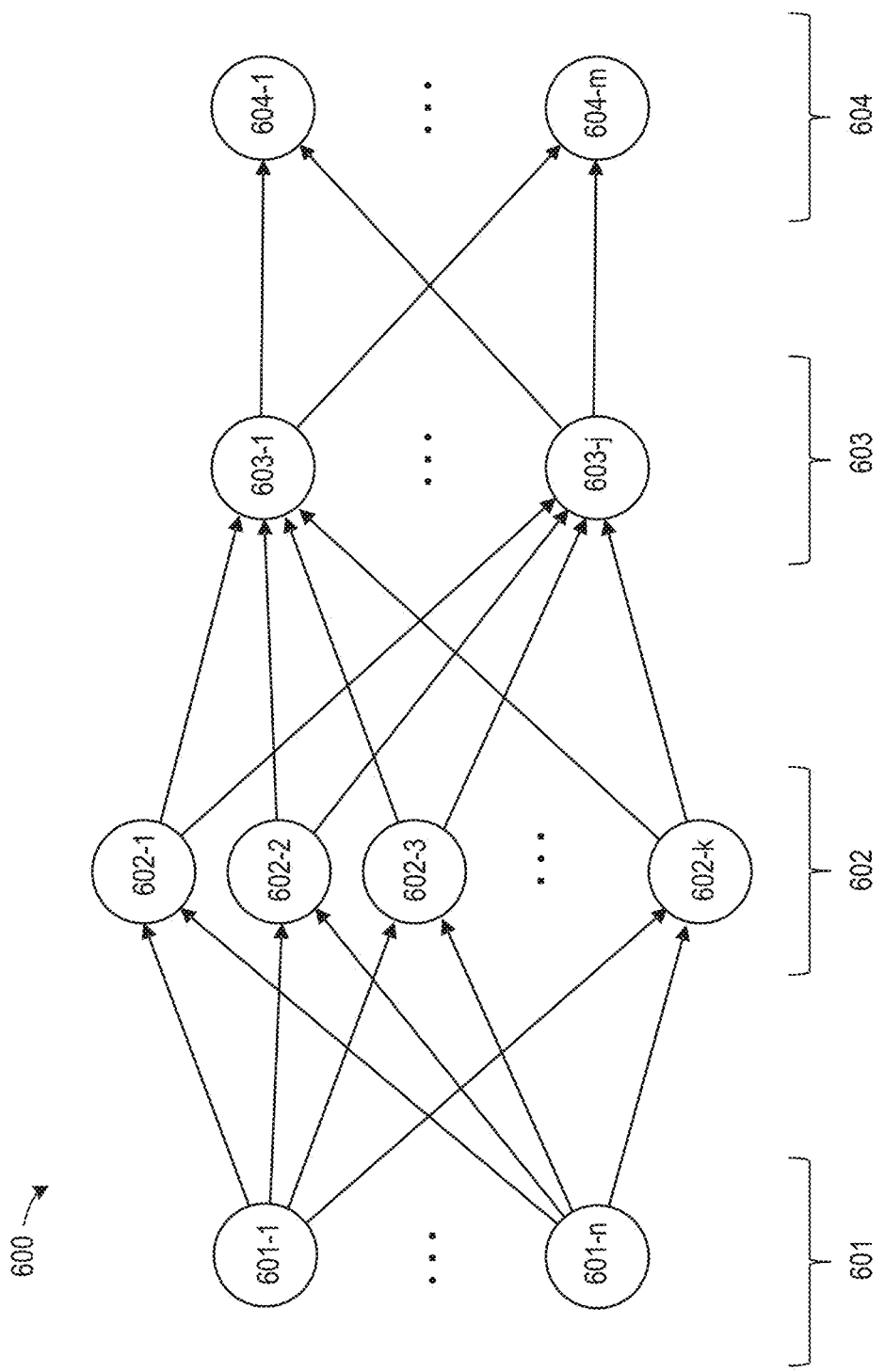
FIG. 6 is a schematic block diagram of a probabilistic neural network (PNN) in accordance with various embodiments.

FIG. 6 is a schematic block diagram of a probabilistic neural network (PNN) 600 that may be used to implement one or more of the machine learning models described herein. In that regard, PNN 600 is a type of feed-forward neural network based on a Bayesian minimum risk criteria, and is advantageous in that it can be trained quickly and has a relatively simple structure. In general, PNN 600 includes an input layer 601 (including nodes 601-1 to 601-n), pattern layer (or "hidden layer") 602 (including nodes 602-1 to 602-n), summation layer 603 (including nodes 603-1 to 603-n), and output layer 604 (including nodes 604-1 to 604-n).

The arrows in FIG. 6 represent the interconnections and weights between the various nodes. Each node in the input layer 601 represents a predictor variable, and pattern layer 602 contains one node for each case in the training data set. PNN 600 is trained, by applying various inputs to input layer 601 and setting output layer 600 to reflect a successfully selected surgery type corresponding to those past survey inputs. PNN 600 does not require training connection weights, but directly configures hidden layer 602 based on the given training samples. In this way, PNN 600 operates in such a way that classifies inputs based on the most similar training data.

Figure 7:
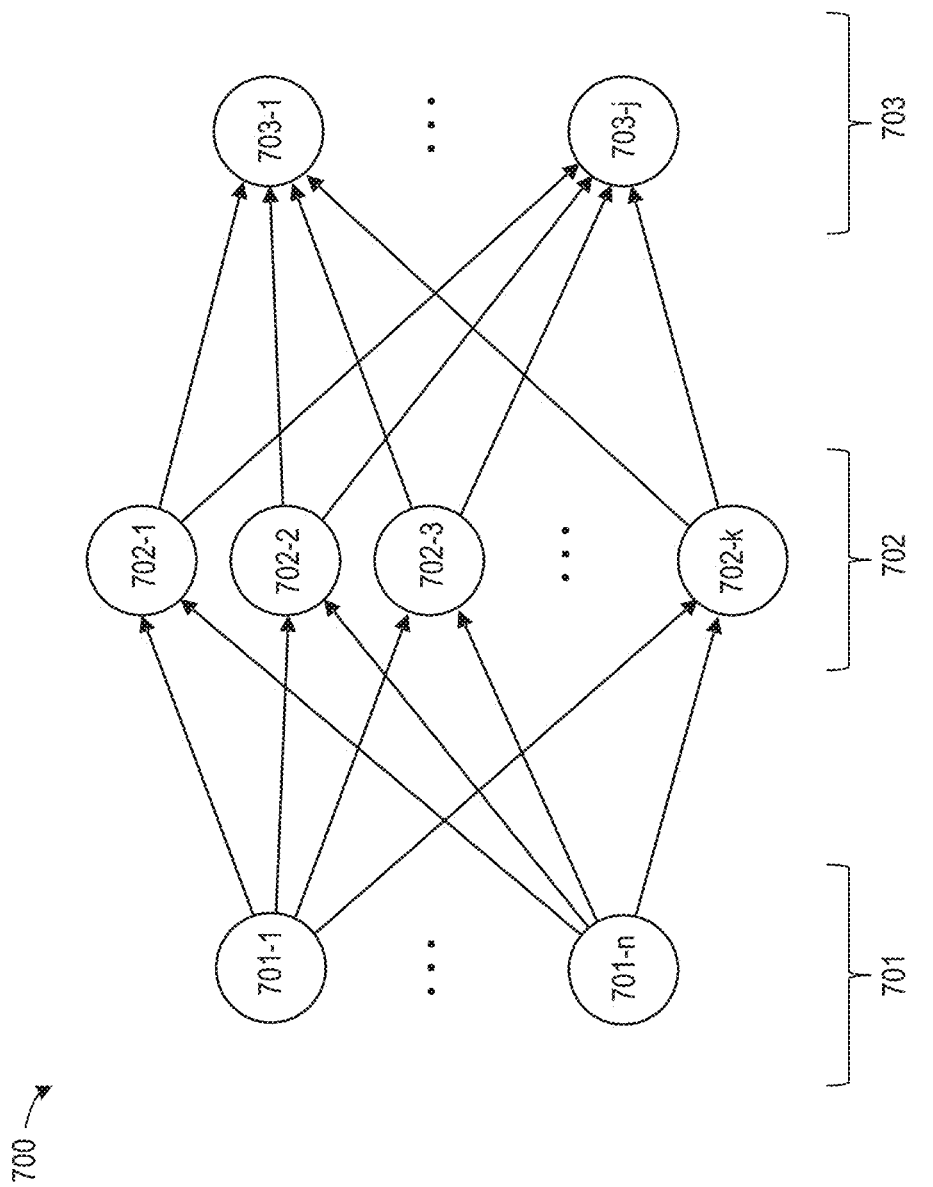
FIG. 7 is a schematic block diagram of an artificial neural network (ANN) in accordance with various embodiments.

FIG. 7 is a schematic block diagram of an artificial neural network (ANN) 700 in accordance with various embodiments. As shown, ANN 700 includes an input layer 701 with a number of input nodes (e.g., 701-1 to 701-n), an output layer 703 with a number of output nodes (e.g., 703-1 to 703-j), and one or more interconnected hidden layers 702 (in this example, a single hidden layer 702 including nodes 702-1 to 702-k).

The number of nodes in each layer (n, k, and j) may vary depending upon the application, and in fact may be modified dynamically by the system itself to optimize its performance. In some embodiments (e.g., deep learning systems), multiple hidden layers 702 may be incorporated into ANN 700.

Each of the layers 702 and 703 receives input from a previous layer via a network of weighted connections (illustrated as arrows in FIG. 7). That is, the arrows in FIG. 7 may be represented as a matrix of floating point values representing weights between pairs of interconnected nodes. Each of the nodes implements an "activation function" (e.g., sigmoid, tanh, or linear) that will generally vary depending upon the particular application, and which produces an output that is based on the sum of the inputs at each node.

ANN 700 is trained via a learning rule and "cost function" that are used to modify the weights of the connections in response to the input patterns provided to input layer 701 and the training set provided at output layer 703, thereby allowing ANN 700 to learn by example through a combination of backpropagation and gradient descent optimization. Such learning may be supervised (with known examples of past survey inputs and surgery outcomes provided to input layer 701 and output layer 703), unsupervised (with uncategorized examples provided to input layer 701), or involve reinforcement learning, where some notion of "reward" is provided during training.

Once ANN 700 is trained to a satisfactory level (e.g., without overtraining), it may be used as an analytical tool to make predictions and perform "classification" of the input 701. That is, new inputs are presented to input layer 701, where they are processed by the middle layer 702 and, via forward propagation through the weights associated with each of the edges, produce an output 703. As described above, output layer 703 will typically include a set of confidence levels or probabilities associated with a corresponding number of different classes, such as the appropriateness of a particular medical intervention.

Figure 8:
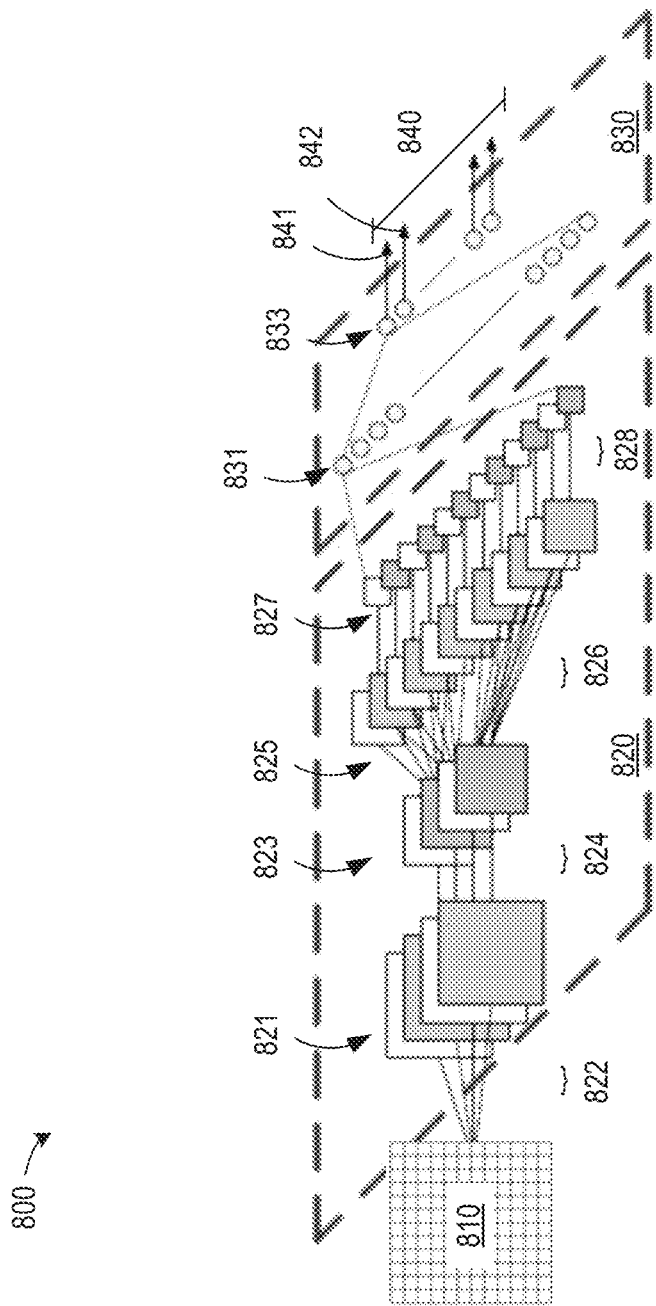
FIG. 8 is a schematic block diagram of a convolutional neural network in accordance with various embodiments.

FIG. 8 is a block diagram of an exemplary convolutional neural network (CNN) in accordance with various embodiments, and which may be used, for example, to process the various images produced as normalized data 120 in FIG. 1 (e.g., X-rays, CT/MRI images, and the like).

As shown in FIG. 8, CNN 800 generally receives an input image 810 (e.g., an X-ray, CT, or MRI image) and produces a series of outputs 840 associated with whether and to what extent certain features are recognized within the image. In that regard, input 810 will be referred to without loss of generality as an "image," even though it might include a variety of sensor data types.

In general, CNN 800 implements a convolutional phase 822, followed by feature extraction 820 and classification 830. Convolutional phase 822 uses an appropriately sized convolutional filter that produces a set of feature maps 821 corresponding to smaller tilings of input image 810. As is known, convolution as a process is translationally invariant—i.e., features of interest (bone geometry, X-ray features, etc.) can be identified regardless of their location within image 810.

Subsampling 824 is then performed to produce a set of smaller feature maps 823 that are effectively "smoothed" to reduce sensitivity of the convolutional filters to noise and other variations. Subsampling might involve taking an average or a maximum value over a sample of the inputs 821. Feature maps 823 then undergo another convolution 828, as is known in the art, to produce a large set of smaller feature maps 825. Feature maps 825 are then subsampled to produce feature maps 827.

During the classification phase (830), the feature maps 827 are processed to produce a first layer 831, followed by a fully-connected layer 833, from which outputs 840 are produced. For example, output 841 might correspond to the likelihood that a particular feature has been recognized.

In general, the CNN illustrated in FIG. 8 trained in a supervised mode by presenting it with a large number (i.e., a "corpus") of input images, such as X-ray, MRI, and CT images (801) and "clamping" outputs 840 based on which features are present within the scene. Backpropagation as is known in the art is then used to refine the training CNN 800. Subsequently, during normal operation, the trained CNN is used to process images 810 as described above.

Figure 9:
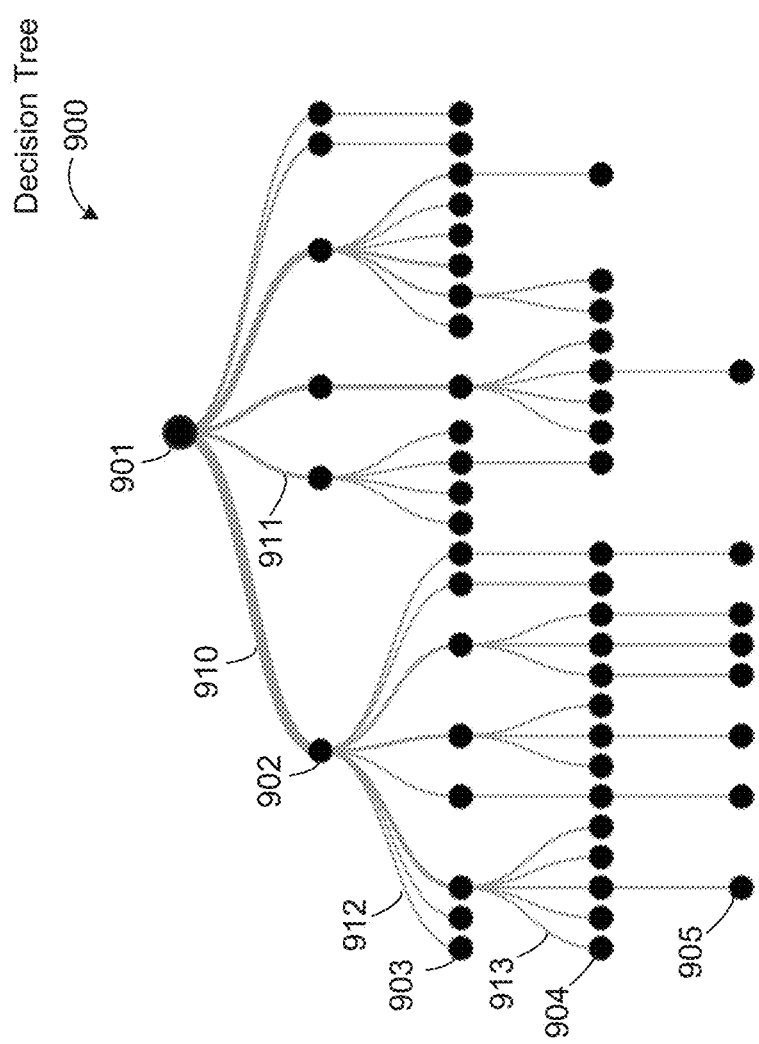
FIG. 9 is a schematic block diagram of a decision tree in accordance with various embodiments.

FIG. 9 is a schematic block diagram of a decision tree in accordance with various embodiments, and which may be used to implement one or more of the machine learning modules illustrated in FIGS. 1 and 2. In general, decision tree 900 is a series of nodes (901, 902, 903, etc.) configured as a directional graph that starts at the root with a single node (901) and extends to the many leaf nodes (e.g., 903, 904, 905) that represent the categories that the tree can classify. Stated another way, decision tree 900 can be seen as a flow chart that starts at the root node 901 and ends with a decision made at the leaves (903, 904, 905, etc.) based on predictions that result from a series of feature-based splits. Root node 901 represents the entire population being analyzed. From the root node, the population is divided according to various features, and those sub-groups are split in turn at each decision node (e.g., 902) under the root node 901. A tree 900 is grown and trained through splitting and "pruning." As is known, one advantage of a decision tree such as that shown in FIG. 9 is that (unlike ANNs) the output of a decision tree is interpretable and understandable by human beings intuitively, and does not require statistical knowledge for interpretation. Decision trees allow analysts to identify significant variables and important relations between two or more variables, helping to surface the signal contained by many input variables. Decision trees are also resilient to outliers and missing values, and require less data cleaning than many other machine learning systems.

While the above discussion often focuses on the use of artificial neural networks, the range of embodiments are not so limited. Any of the various modules described herein may be implemented as one or more machine learning models that undergo supervised, unsupervised, semi-supervised, or reinforcement learning and perform classification (e.g., binary or multiclass classification), regression, clustering, dimensionality reduction, and/or such tasks. Examples of such models include, without limitation, artificial neural networks (ANN) (such as a recurrent neural networks (RNN) and convolutional neural network (CNN)), decision tree models (such as classification and regression trees (CART)), ensemble learning models (such as boosting, bootstrapped aggregation, gradient boosting machines, and random forests), Bayesian network models (e.g., naive Bayes), principal component analysis (PCA), support vector machines (SVM), clustering models (such as K-nearest-neighbor, K-means, expectation maximization, hierarchical clustering, etc.), linear discriminant analysis models.

Figure 10:
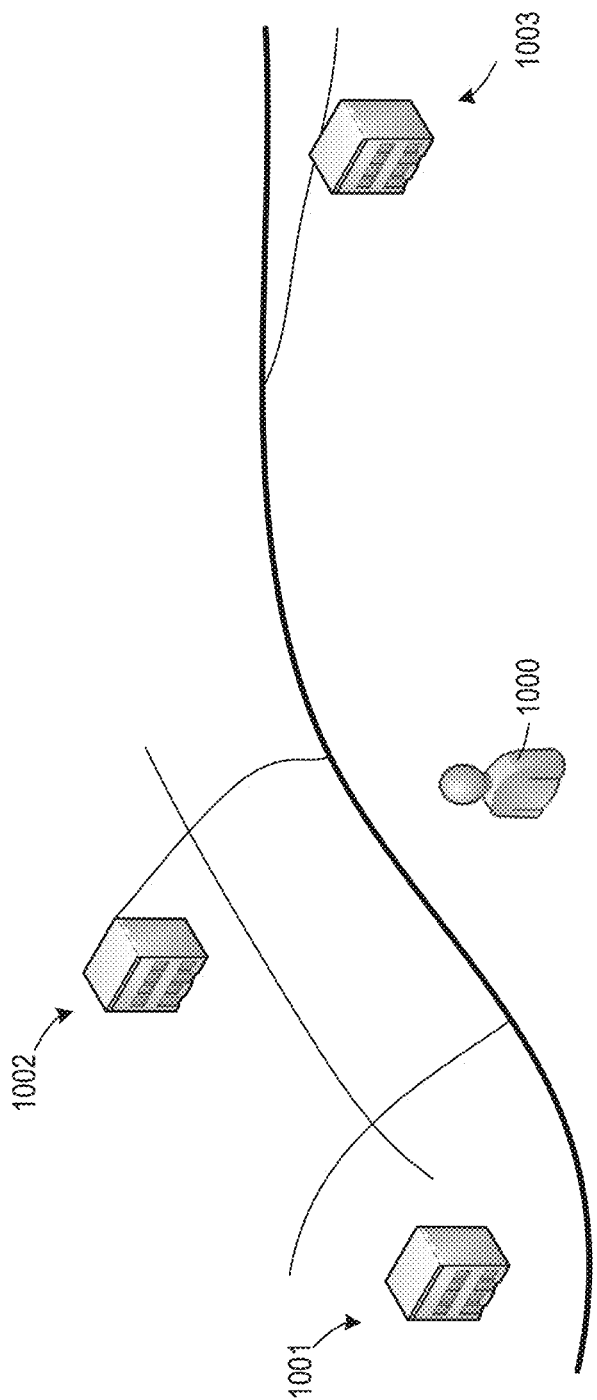
FIG. 10 illustrates the determination of a preferred health care provider based in part on geographical proximity.

In accordance with various embodiments, the output 150 of FIG. 1 and or the outcome outputs 250 of FIG. 2 can be used to determine whether a particular healthcare provider, surgeon, etc. is appropriate for a given type of medical intervention. For example, FIG. 10 illustrates the determination of a preferred health care provider based in part on geographical proximity. Specifically, a patient 1000 may be geographically located closer to a pair of healthcare providers 1001, 1002 than to a third healthcare provider 1003. Nevertheless, the output 150 of system FIG. 1, or the outputs 250 of FIG. 2, may indicate that third healthcare provider 1003 is preferred, despite the fact that it is more geographically remote.

In other embodiments, the outputs 150, 250 may be used to determine which surgeons perform a particular procedure at a satisfactory level as to remain within a contracted (network) group of physicians. In another embodiment, the outputs 150, 250 may be used to determine which health care facilities perform a particular procedure with the best outcomes. In yet another embodiment, the outputs 150, 250 are used to determine which facilities perform a particular procedure at a level that sufficient to remain within a contracted group.

In summary, a machine learning system for determining the appropriateness of a selected medical intervention generally includes a plurality of health-related data sources, the health-related data sources providing at least one data file of a first type, and a second data file of a second type; a normalization module configured to receive the first and second data files and perform a normalization procedure on at least one of the first and second data files, a previously trained machine learning model configured to receive the normalized data files and produce a prediction output, wherein the prediction output includes a confidence level associated with an appropriateness of the selected medical intervention.

The machine learning model may include, for example, an artificial neural network, a probabilistic neural network, a convolutional neural network, or a decision tree.

In various embodiments, the first data file is a two-dimensional image file, and the normalization procedure includes producing an input vector based on the two-dimensional image file. In various embodiments, the two-dimensional image file is selected from the group comprising an X-ray image, a cat-scan (CT) image, and a magnetic resonance image (MRI). In various embodiments, the first data file is a time-varying real value parameter, and the normalization procedure produces an input vector based on the time-varying real value parameter.

In one embodiment, the time-varying real value parameter is a heart-beat audio file. In another embodiment, the time-varying real parameter is a spoken utterance.

In one embodiment, the first data file is a text file, and the normalization procedure includes producing an input vector by applying natural language processing (NLP) to the text file.

In one embodiment, the prediction output is further processed to determine a selected health-care provider for the selected medical intervention.

In one embodiment, the data sources are selected from the group consisting of diagnostic image sources, radiological reports, lab studies, exam findings, survey results, and office notes.

The various systems, modules, and methods described above may be implemented in software using any convenient general-purpose programming language. Suitable languages include, without limitation, web assembly (Wasm), Python, C++, C#, Java, PHP, and the like. In addition, various standard machine learning libraries and linear algebra libraries may be employed.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein is merely exemplary embodiments of the present disclosure. Further, the connecting lines shown in the various figures contained herein are intended to represent example functional relationships and/or physical couplings between the various elements. It should be noted that many alternative or additional functional relationships or physical connections may be present in an embodiment of the present disclosure.

As used herein, the term "module" refers to any hardware, software, firmware, electronic control component, processing logic, and/or processor device, individually or in any combination, including without limitation: application specific integrated circuits (ASICs), field-programmable gate-arrays (FPGAs), dedicated neural network devices (e.g., Google Tensor Processing Units), electronic circuits, processors (shared, dedicated, or group) configured to execute one or more software or firmware programs, a combinational logic circuit, and/or other suitable components that provide the described functionality.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A machine learning system for determining the appropriateness of a selected medical intervention, the system comprising:
a plurality of health-related data sources, the health-related data sources providing at least one data file of a first type, and a second data file of a second type;
a normalization module, including a processor, configured to receive the first and second data files and perform a normalization procedure on at least one of the first and second data files; and
a previously trained machine learning model configured to receive the normalized data files and, via the processor, produce a prediction output, wherein the prediction output includes a confidence level associated with an appropriateness of the selected medical intervention, wherein the previously trained machine learning model is trained based on a population of patients that have previously undergone the selected medical intervention, wherein the training utilizes, as a training parameter, a jury-produced determination of the appropriateness, in the form of a numeric appropriateness value, of the selected medical intervention, and the medical intervention corresponds to a form of surgery;
wherein the prediction output is used during an insurance utilization review to produce a Boolean determination of whether to perform the selected medical intervention on a particular patient.

2. The machine learning system of claim 1, wherein the at least one machine learning model is an artificial neural network.

3. The machine learning system of claim 1, wherein the at least one machine learning model is a probabilistic neural network.

4. The machine learning system of claim 1, wherein the at least one machine learning model is a convolutional neural network.

5. The machine learning system of claim 1, wherein the at least one machine learning model is a decision tree.

6. The machine learning system of claim 1, wherein the first data file is a two-dimensional image file, and the normalization procedure includes producing an input vector based on the two-dimensional image file.

7. The machine learning system of claim 6, wherein the two-dimensional image file is selected from the group comprising an X-ray image, a cat-scan (CT) image, and a magnetic resonance image (MRI).

8. The machine learning system of claim 1, wherein the first data file is a time-varying real value parameter, and the normalization procedure produces an input vector based on the time-varying real value parameter.

9. The machine learning system of claim 8, wherein the time-varying real value parameter is a heart-beat audio file.

10. The machine learning system of claim 8, wherein the time-varying real parameter is a spoken utterance.

11. The machine learning system of claim 1, wherein the first data file is a text file, and the normalization procedure includes producing an input vector by applying natural language processing (NLP) to the text file.

12. The machine learning system of claim 1, wherein the prediction output is further processed to determine a selected health-care provider for the selected medical intervention.

13. The machine learning system of claim 1, wherein the data sources are selected from the group consisting of diagnostic image sources, radiological reports, lab studies, exam findings, survey results, and office notes.

14. A method for determining the appropriateness of a selected medical intervention utilizing a machine learning system, the method comprising:
receiving, from a plurality of health-related data sources, at least one data file of a first type, and a second data file of a second type;
performing, with a processor, a normalization procedure on at least one of the first and second data files; and
applying at least one previously trained machine learning model to the normalized data files to produce a prediction output; wherein the prediction output includes a confidence level associated with an appropriateness of the selected medical intervention, wherein the previously trained machine learning model is trained based on a population of patients that have previously undergone the selected medical intervention, wherein the training utilizes, as a training parameter, a jury-produced determination of the appropriateness, in the form of a numeric appropriateness value, of the selected medical intervention, and the medical intervention corresponds to a form of surgery;
using the prediction output during an insurance utilization review to produce a Boolean determination of whether to perform the selected medical intervention on a particular patient.

15. The method of claim 14, wherein the at least one machine learning model is an artificial neural network.

16. The method of claim 14, wherein the at least one machine learning model is a probabilistic neural network.

17. The method of claim 14, wherein the at least one machine learning model is a convolutional neural network.

18. The method of claim 14, wherein the at least one machine learning model is a decision tree.

19. The method of claim 14, wherein the first data file is a two-dimensional image file, and the normalization procedure includes producing an input vector based on the two-dimensional image file.

20. The method of claim 19, wherein the two-dimensional image file is selected from the group comprising an X-ray image, a cat-scan (CT) image, and a magnetic resonance image (MRI).

* * * * *